Figure 1:
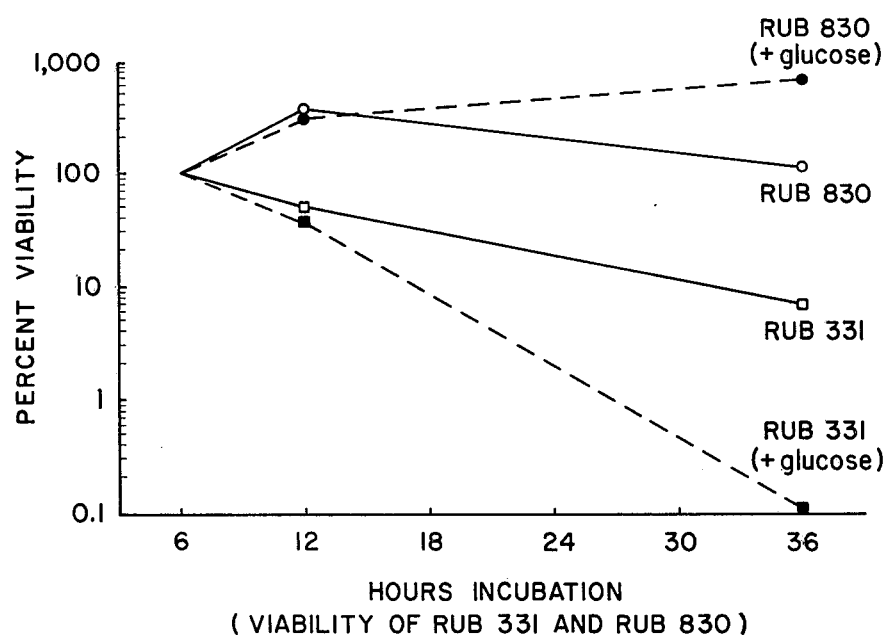

United States Patent [19]

Young et al.

[11] 4,302,544

[45] Nov. 24, 1981

[54] **ASPOROGENOUS MUTANT OF *B. SUBTILIS* FOR USE AS HOST COMPONENT OF HV1 SYSTEM**

[75] Inventors: Frank E. Young, Pittsford; Gary A. Wilson; Susan L. Mottice, both of Rochester, all of N.Y.

[73] Assignee: University of Rochester, New York, N.Y.

[21] Appl. No.: 84,595

[22] Filed: Oct. 15, 1979

[51] Int. Cl.³ .......................... C12N 1/20; C12N 15/00
[52] U.S. Cl. .................................. 435/253; 435/172; 435/839
[58] Field of Search ...................... 435/172, 253, 839

[56] References Cited

PUBLICATIONS

Frobisher, Fundamentals of Microbiology 9th Ed. pp. 265–270 (1974).

*Primary Examiner*—Alvin E. Tanenholtz
*Attorney, Agent, or Firm*—James D. McNeil

[57] ABSTRACT

Asporogenous mutant *B. subtilis* RUB 331 (ATCC 31578) and a process for using such mutant are disclosed. The asporogenous mutant desirably reverts to sporeformers with a frequency not greater than $10^{-7}$ reversions per bacterium per generation and meets the requirements of the NIH "Guidelines for Research Involving Recombinant DNA Molecules" for a *B. subtilis* host component of a Host-Vector 1 system.

1 Claim, 1 Drawing Figure

ASPOROGENOUS MUTANT OF B. SUBTILIS FOR USE AS HOST COMPONENT OF HV1 SYSTEM

BACKGROUND AND PRIOR ART OF THE INVENTION

It is well known that the genetic information of all cells is stored in deoxyribonucleic acid (DNA) in the chromosomal material of organisms. The units of genetic function, i.e., the locus on the chromosome related to a specific hereditary trait, is called a gene.

Recombinant DNA technology involves the transfer of genetic material (genes) from one organism into a second organism and the propagation of these combined materials in bacterial and animal cells. The cell into which the recombinant genetic material is inserted is designated the host.

In the 1950's it was discovered that bacterial cells contain circular extra chromosomal DNA molecules, called plasmids, in addition to the main DNA molecule. The plasmids contain a series of genes, linked together in the form of a circle. These plasmids are small, easy to handle in the laboratory and enter other bacteria with ease. Plasmids represent a class of DNA molecules which accept DNA fragments and are referred to as the vector component of the hostvector system. Subsequently it was discovered that bacterial cells contain restriction enzymes that act as "chemical scalpels" to split DNA molecules into specific fragments which usually contain from less than 1 to 10 genes each. These specific fragments are the genetic material that will be inserted into the vector. The combined DNA fragment and vector are referred to as recombinant DNA. Restriction enzymes cleave viral DNA in the same manner as they cleave the plasmid DNA. Viruses represent another class of vectors.

Using recombinant DNA technology, genetic exchange between bacteria can be accomplished as follows. Plasmid or viral DNA (vector) is first isolated. Plasmid DNA is then linearized by cleaving or breaking the molecule at a single site, either by the use of restriction enzymes or other means. The DNA to be inserted (for example chromosomal) into the vector is also cleaved with restriction enzymes or other well known techniques designed to break the DNA into fragments. A fragment for the desired genetic characteristic is then inserted into the "broken" plasmid (the vector DNA ring). By treatment with DNA ligase the ends are joined and a recombinant plasmid DNA molecule is formed. The recombinant plasmid DNA molecule contains the genes of the bacterial plasmid plus the new genes from the inserted fragment. This plasmid can be introduced into a bacterium host. The new genes are propagated and become a part of the genetic machinery of the bacterium. In order to be useful for recombinant DNA technology, the microorganism (host) must be capable of undergoing "transformation", i.e., itself be capable of incorporating DNA and yielding a viable microorganism capable of expressing the traits encoded by the newly inserted genes. In this way the microorganism (host) can incorporate other desirable generic characteristics from other organisms.

It has been clear from the beginning of experimentation in recombinant DNA technology that novel gene combinations may have a potential for biological hazard, in that novel microorganisms capable of releasing products harmful for man, plants, or animals, may be produced. In order to prevent the spread of potentially harmful microorganisms, appropriate containment safeguards were investigated.

Containment of potentially biohazardous agents can be achieved in several ways. In 1978, the Direction of the NIH issued "Guidelines for Research Involving Recombinant DNA Molecules" (FR 43 60108) which set forth containment provisions. Physical containment was approached by using a set of microbiological standards which have been developed over a period of years for handling pathogenic organisms in research and clinical laboratories.

An equally important containment approach, because it contributes most significantly to limiting the spread of any potentially biohazardous agent, is the use of biological containment safeguards. Biological containment can be defined as the use of host cells and vectors with limited ability to survive outside of very special and fastidious conditions which can be maintained in the laboratory but are unlikely to be encountered by escaped organisms in natural environments.

The NIH Guidelines established levels of biological containment for host-vector systems (designated HV), dependent upon the microorganism and the DNA used. HV1 is defined as a "host-vector system which provides a moderate level of containment."

In 1979, the NIH issued "Actions" (FR 44 71) under the NIH Guidelines which included criteria for consideration of B. subtilis for certification as a host in a HV1 system. The FR Action stated that:

"Asporogenic mutant derivatives of B. subtilis can be accepted as the host component of an HV1 system. These derivatives must not revert to sporeformers with a frequency greater than $10^{-7}$; data confirming this requirement must be presented to NIH for certification."

Emphasis was placed on eliminating formation of spores by the mutants because certain Bacillus species have developed a specialized mechanism for survival which involves the formation of spores. Spores are in a state of latent life with no metabolic activity and an increased resistance to the lethal effect of heat, drying, freezing, deleterious chemicals and radiation. In order to be susceptible to biological containment, Bacillus microorganisms cannot be capable of functioning as efficient sporeformers.

The present invention describes a new asporogenous mutant of B. subtilis RUB 830 designated as B. subtilis RUB 331, (ATCC 31578) and a process for using it in a host-vector system.

The literature on sporulation and the formation of mutants is extensive. Formation of mutants, including asporogenous mutants, is described in Bacteriological Reviews, Vol. 33:48-71 (1969) and Vol. 40:908-962 (1976). Also J. Bacteriol. 81:823-829 (1961) describes transformation of B. subtilis. These references do not disclose production of an asporogenous mutant which has the phenotype characteristics of the present invention.

SUMMARY OF THE INVENTION

The present invention is directed to a new asporogenous B. subtilis mutant, which meets the certification requirements of NIH as a host in a HV1 system and a method of using such mutant in a HV1 system. The mutant was produced by incorporating donor DNA in a spore-forming Bacillus subtilis strain and obtaining therefrom said asporogenous *B. subtilis* having the following characteristics: translucent phenotype on tryptose blood agar plates but not on Spizizen's minimal agar supplemented with glucose; a frequency of transformation with linear or covalently closed circular DNA of up to 2 percent; lyses in a complex medium; viability reduced to 0 CFU/ml after drying at room temperature for about 12 hours and frequency of reversion to sporeformers of less than $10^{-7}$, under conditions of minimal aeration and the described growth medium.

DESCRIPTION OF THE INVENTION

The *B. subtilis* disclosed and claimed has been deposited with the American Type Culture Collection, Rockville, Maryland and has been given the following identification number: ATCC 31578. This culture is available to the public without restriction. The parental strain has been described earlier and both RUB 830 [Williams, M. T. and Young, F. E., *J. Virol* 21:522-529 (1977)] and *B. subtilis* 168T+ [Bott, K. F. and Wilson, G. A., *Bacteriol. Reviews* 32:370-378 (1968)]; [Wilson, G. A. and Young, F. E., *J. Bacteriol.* 111:705-716 (1972)] have been available to the public from the personal collection of the investigators.

The asporogenous strain of the present invention is a highly transformable strain with frequencies of up to 2 percent. The transformation can be effected by either plasmid or chromosomal DNA. Frequency of reversion to spore-formers is less than $10^{-7}$. The strain exhibits marked susceptibility to the effects of drying at room temperature as compared with spore-forming Bacillus. Under sporulation conditions when the parent exhibits 20-80 percent sporulation, no sporulation has been observed in the mutant strain. In addition, when grown under conditions required for sporulation of the parent strain as described in this disclosure, 90 percent of the mutant strain becomes nonviable.

*Bacillus subtilis* RUB 331 (ATCC 31578) was produced from *B. subtilis* RUB 830 by incorporating DNA from *B. subtilis* 168T+ (wild-type) according to the following procedure.

EXAMPLE

Transformation of the parent spore-forming RUB 830 (pheA1, trpC2,thyA1, thyB1) strain into the instant asporogenous strain RUB 331 by incorporation of DNA obtained from the *B. subtilis* 168T+ (wild-type) i.e., Phe+, Trp+, Thy+, was carried out as follows.

*B. subtilis* RUB 830 was incubated overnight in a growth medium (designated GM1) at 32° C. GM1 contained: 10 ml Spizizen's minimal medium supplemented with 22 mM glucose, 0.02% acid-hydrolyzed casein, 0.1% yeast extract and 500 µg each of phenylalanine, tryptophane and thymidine. Spizizen's minimal medium is a solution of (a) ammonium sulfate—0.2 percent; (b) potassium phosphate-dibasic—1.4 percent; (c) potassium phosphate-monobasic—0.6 percent; (d) sodium citrate-0.1 percent and (e) magnesium sulfate-0.02 percent; pH adjusted to 7.4 [Spizizen, J., *Proceedings National Academy of Sciences*, 44:1072-1078 (1958)]. The RUB 830 was diluted two-fold with fresh GM1 twelve hours later and incubation was continued at 37° C. until the culture reached a stationary phase of growth. Ninety minutes later, the culture was diluted 10-fold into a growth medium designated as GM2. GM2 is similar to GM1 except that $CaCl_2$ and $MgCl_2$ were added to bring the final concentrations to 5 and 2.5 mM, respectively. Incubation was continued for 60 minutes before donor DNA was added.

Donor DNA was obtained from *B. subtilis* 168T+ (wild type), by the following procedure.

The wild strain of *B. subtilis* utilized for donor DNA was grown in a peptone medium, commercially available from Difco Laboratories, Detroit, Michigan, under the trade designation Difco Penassay Broth. After 12 hours of incubation with shaking at 37° C., the cells were harvested by centrifugation and washed twice with and resuspended in a buffer which consisted of a solution of 20 mM of tris(hydroxymethyl)aminomethane, commercially available from Sigma Chemical, St. Louis, Missouri, under the trade designation Trizma Base, and 20 mM ethylenediamine tetraacetic acid (EDTA) at a pH of 7.0.

The cell suspension was lysed by incubation with crystalline egg white lysozyme (1 mg per ml) for 30 minutes at 37° C. Protein was removed from the lysate by treatment with sodium lauryl sulfate (final concentration 1%) for 1 hour at 37° C. DNA was precipitated with 70 percent cold ethanol and suspended in a solution containing 10 mM Trizma Base and 1 mM EDTA at a pH of 7.4. It is known that spore mutations occur near the region of the chromosome that encodes the phenylalanine biosynthetic enzymes; the following procedure was used to transform the RUB 830 microorganism.

A 0.1 ml sample of DNA solution was added to 0.9 ml of RUB 830 culture and incubated for 30 minutes at 37° C. with aeration. The cells were diluted in Spizizen's minimal medium. Samples (0.1 ml) were spread on plates of Spizizen's minimal agar (supplemented with 22 mM glucose, 1 mg/plate thymidine and 0.4 mg/plate tryptophan) in order to select cells transformed to phenylalanine independence, (Phe+).

Colonies that were transformed to phenylalanine independence were observed that were either hyperpigmented (red-brown) or non-pigmented (whitish) in contrast to the level of pigmentation (brown) observed in the parent. These colonies were isolated by subculturing to individual plates containing the same medium as described above and further growth allowed to take place. Colonies were also subcultured and grown on a peptone medium of tryptose blood agar plates (TBAB). Media such as TBAB or peptone are not chemically defined and are referred to as "complex" media. The TBAB plates were prepared from an agar base commercially available from Difco Laboratories, under the trade designation Bacto-Tryptose Blood Agar Base. These colonies gave a characteristic translucent phenotype of asporogenous strains on tryptose blood agar plates (TBAB) but not on Spizizen's minimal agar with glucose [See *Bacteriological Reviews*, Vol. 40:908-962 (1976)].

Both the non-pigmented mutations and the hyperpigmented mutations were asporogenic. The non-pigmented isolates appeared to be less hardy than the hyperpigmented isolates. One hyperpigmented isolate was selected and designated RUB 331. The genotype of this strain is trpC2, thyA1, thyB1, spo-331.

Evaluation of *B. Subtilis* RUB 331

I. Transformation Frequency

In order to function effectively as a host in recombinant DNA work, the host microorganism must be transformable, i.e., have the ability to incorporate DNA to form viable mutant organisms. The microorganism of the present invention can be transformed with both linear and covalently closed circular DNA.

Transformation frequencies of above 0.01 percent have been found acceptable in the prior art. In producing asporogenic mutants, it has generally been found that the percent of transformation obtainable decreases. Generally, transformable strains remain resistant to lysing in a complex medium. This resistance is undesirable, since the ability to lyse will minimize dissemination of the microorganism from a laboratory environment. As described hereinafter, RUB 331 strain lyses readily in a complex medium, thus combining the desirable traits of lysing and asporogeny with a high rate of transformation.

The transformation frequency was determined by using both DNA from *B. subtilis* 168T+ (0.5–2.0 μg/ml), which is linear, and circular chimeric plasmid pCD1 (0.1–65 μg/ml) as sources of the donor DNA, and measuring the number of viable new cells formed by selecting a genetic "marker" that can be quantitatively measured.

(a) Transformation with Linear DNA

The linear DNA from *B. subtilis* 168T+ (wild-type) was isolated as described previously in the preparation of RUB 331. The transformation of RUB 331 by incorporation of DNA from *B. subtilis* 168T+ (wild-type) was carried out by the same procedure as described earlier with the exception that selection was for thymidine independence by omitting thymidine from the growth medium.

The frequency of transformation was determined by plating a sample of the culture on growth medium with and without thymidine. The frequency of transformation represents the ratio of the number of colonies which required thymidine for growth and the number of colonies of transformed cells which did not require thymidine due to the incorporation of the gene encoding thymidylate synthetase.

Using this technique, the following transformation frequencies were obtained.

TABLE I

| Source of Transforming DNA | Percent Transformation DNA Concentration | % Transformation to Thymidine Independence |
|---|---|---|
| *B. subtilis* 168T+ | 0.5 μg/ml | .01 |
| *B. subtilis* 168T+ | 1.0 μg/ml | 0.1 |
| *B. subtilis* 168T+ | 20.0 μg/ml | 1.1 |

(b) Transformation with Circular DNA

Plasmid pCD1 was used as a source of circular DNA. The isolation and structure of this plasmid is described in Gene. 1:153–167 (1977). The transformation procedure used and determination of frequency of transformation was identical to that described above for the linear DNA.

The following transformation frequencies were obtained.

TABLE II

| Source of Transforming DNA | Percent Transformation DNA Concentration | % Transformation to Thymidine Independence |
|---|---|---|
| pCD1 | 0.1 μg/ml | 0.04 |

TABLE II-continued

| Source of Transforming DNA | Percent Transformation DNA Concentration | % Transformation to Thymidine Independence |
|---|---|---|
| pCD1 | 0.5 μg/ml | 0.35 |
| pCD1 | 65.0 μg/ml | 2.00 |

These results summarized in Tables I and II indicate that even at low concentrations of DNA, RUB 331 is suitable for use as a mutant capable of undergoing transformation.

II. Viability

A favorable characteristic for a microorganism suitable for use as a host component of a host-vector system is that it have limited survival capabilities if the microorganism were to escape into the environment. Even under the most favorable growth conditions, RUB 331 has little potential for survival in comparison to the parental strain. This was tested directly by comparing the viability of RUB 331 to the viability of the parent RUB 830 by growing the cells in a favorable growth medium, as follows. Cells were grown in a broth ("M broth") which is composed of a peptone and yeast extract. M broth was produced by mixing together 10 g Difco tryptone, 5 g Difco yeast extract and 9.9 g sodium chloride per liter of distilled water, supplemented with $10^{-4}$ M ferric nitrate. Viability was determined in this medium and compared with viability in the same medium with glucose added. As described below, viability was assayed on TBAB plates supplemented with 2 mg/plate thymidine. Viability is reported as "colony forming units/ml" (CFU/ml).

For each culture, viabilities were normalized to 100 percent of the 6 hour value. The 6 hour values for strain RUB 331 was $5.1 \times 10^7$ Colony Forming Units (CFU/ml); RUB 331 in glucose was $2.6 \times 10^7$ CFU/ml; RUB 830 was $1.3 \times 10^8$ CFU/ml and for RUB 830 in glucose was $3.0 \times 10^7$ CFU/ml.

FIG. 1 illustrates the viability of RUB 830 and RUB 331, after 6, 12 and 36 hours of incubation in M broth [supplemented with $10^{-4}$ M Fe(NO$_3$)$_3$] with and without 0.5 percent glucose added. As seen from FIG. 1, under either of these favorable growth conditions viability of RUB 331 decreases rapidly from a maximum value which usually occurs after 6 to 12 hours incubation. In contrast, the viability of RUB 830 is still increasing after 36 hours in the presence of glucose.

III. Frequency of Reversion to Sporeformers

Many mutants that are impaired in their ability to form spores and that are designated as "asporogenic", do in fact form spores at a low frequency as a result of the "leakiness" of the original mutation. This "leakiness" results in heat resistant spores that retain the original mutation. As a result it is necessary to distinguish between frequency of sporulation ("leakiness") and the frequency of reversion of the mutation, which reflects the stability of the mutation.

In most asporogenous strains it is not possible to measure the reversion frequency, even though this is the criteria required by NIH for certification of a *B. subtilis* as a HV1 host. The mutant strain RUB 331 is unique in that it is possible to measure the reversion frequency independent of the frequency of sporulation. This is made possible because of the colony morphology, i.e., RUB 331 is translucent on TBAB plates and the parent strain or revertants of RUB 331 are not. In all cases studied, the reversion to opaque, large colonies correlated with reversion to sporeforming bacteria.

The reversion frequency was measured by the Newcombe [*Nature London*, 164:150; (1946)] spreading technique since this technique has several advantages. Not only is it appealingly simple, but it also is not affected by differences in growth rate between mutant and wild type bacteria. Although the mutant strain has a translucent appearance on complex medium, it is necessary to determine if wild type clones would be distinguishable in the presence of a confluent growth of mutant bacteria. To test this, mutant and wild type bacteria were mixed in various proportions. Opaque wild type colonies were clearly distinguishable when plated in the presence of $1.5 \times 10^6$ or $1.5 \times 10^3$ mutant translucent RUB 331 cells. In addition, there was no difference between the number of wild type cells observed in the control plates that were plated without mutant cells and those that were plated with mutant cells. These results indicated that mutant cells did not cause the lysis of wild type cells and clearly established that the Newcombe method could be used to estimate the reversion frequency.

Cells were routinely plated on TBAB plates and incubated at 37° C. for 5 hours. At this time one series of plates was respread with 0.1 ml minimal salts and reincubated overnight. Sixty minutes later, another series of plates was respread and reincubated. The increase in viability between 5 and 6 hours was determined by suspending the colonies from representative plates in 2 ml of minimal salts and the resulting dilutions plated. The mutation rate (or reversion rate) was derived from the following formula (Newcombe).

$$m = \log_e 2 \frac{(M_2 - M_1)}{(N_2 - N_1)}$$

where $M_1$ and $M_2$ are the number of wild type clones arising from plates assayed at 5 and 6 hours, and $N_1$ and $N_2$ are the corresponding total bacteria at these times. From one series of plates where $1.3 \times 10^6$ CPU were initially seeded per plate, the reversion frequency was $7 \times 10^{-10}$. A similar value of $9 \times 10^{-10}$ was observed when plates were seeded with $1.5 \times 10^6$ CFU. These values are well within the limits for frequency of reversion to sporeformers for asporogenic mutant derivatives of *B. subtilis* established by the NIH Recombinant DNA Advisory Committee.

IV. Limits of Asporogeny

Sporulation frequencies were difficult to obtain for strain RUB 331 due to decreasing viability in sporulation media compared to wild-type strains. As discussed hereinbefore, the data shown in FIG. 1 compare the viability of RUB 830 and RUB 331 after 6, 12, and 36 hours of incubation in M broth [supplemented with $10^{-4}$ M Fe(NO$_3$)$_3$] with and without 0.5 percent glucose added. Viability of RUB 331 has not been seen to exceed $2 \times 10^8$ CFU/ml under these conditions and decreases rapidly from a maximum value which usually occurs after 6 to 12 hours incubation. RUB 830, the parental strain, will not sporulate under these conditions in 12 hours, but requires at least 24 hours for 20–100 percent sporulation. Decreasing the amount of aeration during growth of RUB 331, by incubating the strain in a test tube, rather than in an erlenmeyer flask, enabled the determination of sporulation frequencies at 24 hours by slightly inhibiting cell lysis. It was still necessary to centrifuge the cells before plating to ensure that sufficient numbers of the cells were present. It was also necessary to add 1 percent sodium lauryl sulfate to the samples before heating in order to get reproducible estimates of sporulation. This was due to heat-induced coagulation of the cellular debris from the lysed cells that was capable of entrapping and protecting viable cells. This phenomenon is not seen in 12 hour cultures where RUB 331 cell lysis is not yet predominant. The results of the sporulation tests are presented in Table III.

TABLE III

| | Frequency of Sporulation in *Bacillus Subtilis* | | |
|---|---|---|---|
| Strain | Incubation (hours) | Viability (CFU/ml) | Spores |
| RUB 331 | 12 | $4.3 \times 10^9$ | 0 |
| RUB 830 | 12 | $1.3 \times 10^7$ | 0 |
| RUB 331 | 24 | $2.1 \times 10^8$ | 0 |
| RUB 830 | 24 | $3.1 \times 10^8$ | $1.0 \times 10^9$ |
| RUB 331 | 24 | $8.8 \times 10^6$ | 0 |
| RUB 830 | 24 | $2.7 \times 10^8$ | $1.8 \times 10^8$ |

Under conditions where RUB 830 demonstrates a high frequency of sporulation, no sporulation was observed with RUB 331, indicating that RUB 331 lacks the ability to form spores, thus minimizing its potential for undesirable long term survival.

V. Effects of Dessication on Survival

This experiment was designed to simulate a desktop spill of RUB 331 and to estimate the length of time such a spill of RUB 331 would remain viable. Eight hour cultures of RUB 331 or RUB 830 in M broth [supplemented with $10^{-4}$ M Fe(NO$_3$)$_3$] were used to saturate 0.25 inch diameter sterile concentration disks which were then placed in a sterile petri dish at room temperature. These discs were then allowed to dry. Viability was determined at various times by suspending a disk in 1 ml sterile Spizizen's minimal salts and plating on TBAB plates supplemented with 2 mg/plate thymidine.

TABLE IV

| | Effects of Dessication on Survival | | | |
|---|---|---|---|---|
| | RUB 830 | | RUB 331 | |
| Hours Dessication (at desktop) | CFU/ml | % Original Value | CFU/ml | % Original Value |
| 0 | $4.5 \times 10^7$ | 100.0 | $2.5 \times 10^7$ | 100 |
| 6 | $3.8 \times 10^7$ | 84.0 | $6.0 \times 10^6$ | 24 |
| 18 | $2.3 \times 10^5$ | 0.5 | 0 | 0 |
| 36 | $1.6 \times 10^5$ | 0.3 | 0 | 0 |

As shown in Table IV RUB 331 shows an increased susceptibility to the effects of drying at room temperature as compared to the RUB 830 parental strain. The decrease of RUB 331 viability to zero coincides with the complete drying of the concentration disk and therefore represents a minimal hazard of dissemination.

What is claimed is:

1. A biologically pure culture of asporgenous *B. subtilis* RUB 331 (ATCC 31578) suitable for use as a host component in a host-vector system having the following characteristics: translucent phenotype on tryptose blood agar plates but not on Spizizen's minimal agar supplemented with glucose; a frequency of transformation with linear or covalently closed circular DNA of up to 2 percent; lyses in a complex medium; viability reduced to 0 CFU/ml after drying at room temperature for about 12 hours and a frequency of reversion to sporeformers of less than $10^{-7}$, under conditions of minimal aeration.

* * * * *